US00PP20694P3

(12) United States Plant Patent

Mehlenbacher et al.

(10) Patent No.: US PP20,694 P3

(45) Date of Patent: Feb. 2, 2010

(54) *CORYLUS* PLANT NAMED 'RED DRAGON'

(50) Latin Name: *Corylus avellana*
Varietal Denomination: Red Dragon

(75) Inventors: Shawn A. Mehlenbacher, Corvallis, OR (US); David C. Smith, Corvallis, OR (US)

(73) Assignee: The State of Oregon, Acting By and Through the State Board of Higher Education; Oregon State Univ, Corvallis, OR (US)

( * ) Notice: Subject to any disclaimer, the term of this patent is extended or adjusted under 35 U.S.C. 154(b) by 0 days.

(21) Appl. No.: 12/148,080

(22) Filed: Apr. 16, 2008

(65) Prior Publication Data

US 2009/0265820 P1 Oct. 22, 2009

(51) Int. Cl.
*A01H 5/00* (2006.01)

(52) U.S. Cl. ..... Plt./152

(58) Field of Classification Search ..... Plt./152, Plt./226

See application file for complete search history.

*Primary Examiner*—June Hwu

(74) *Attorney, Agent, or Firm*—Dann, Dorfman, Herrell & Skillman; Robert C. Netter

(57) ABSTRACT

A new and distinct cultivar of *Corylus* plant named 'Red Dragon,' characterized by its outwardly spreading plant habit, twisting stems, rich dark burgundy-colored leaves, burgundy color of the catkins and leaf buds, and resistance to eastern filbert blight caused by the fungus *Anisogramma anomala* (Peck) E. Muller.

3 Drawing Sheets

This invention was made with government support under Specific Cooperative Agreement No. 58-5358-4542 awarded by the United States Department of Agriculture. The government has certain rights in the invention.

Latin name of the genus and species of the plant claimed: *Corylus avellana.*

Variety denomination: 'Red Dragon'.

BACKGROUND OF THE INVENTION

The present invention relates to a new and distinct cultivar of *Corylus* plant (hazelnut, filbert), botanically known as *Corylus avellana,* and hereinafter referred to by the name 'Red Dragon'.

The new *Corylus* resulted from a controlled cross of female parent OSU 487.055 and male parent OSU 367.039 made in 1997 by Shawn A. Mehlenbacher and David C. Smith. Neither parent was protected by a plant patent. Hybrid seeds from the cross were harvested in August 1997, stratified, and seedlings grown in the greenhouse during the summer of 1998. From this cross, 42 seedlings with contorted growth habit were planted in the field in October 1998. 'Red Dragon' was discovered and selected by the inventors as a single plant within the progeny of the stated cross-pollination in a controlled environment in Corvallis, Oreg., USA. It was originally assigned the designation OSU 897.078, which indicates the row and tree location of the original seedling.

The female parent OSU 487.055 is from a cross of 'Contorta'×VR 6-28 (which is a cross of 'Riccia di Talanico'× 'Gasaway'), and the male parent OSU 367.039 is a red-leaf selection from open-pollination of 'Contorta.' The presumed pollen parent of OSU 367.039 is the red leaf cultivar 'Rode Zeller' (syn. 'Rote Zellernuss'), which has a dominant allele at the leaf anthocyanin locus. A tree of 'Rode Zeller' was near the 'Contorta' tree from which open-pollinated nuts were collected. 'Red Dragon' and OSU 487.055 carry in heterozygous state a dominant allele for complete resistance to eastern filbert blight (EFB) from 'Gasaway.' Contorted growth habit is conferred by a recessive allele from 'Contorta' (syn. *Corylus avellana* var. *contorta*).

The new cultivar was asexually reproduced by rooted suckers (tie-off layerage of the suckers) annually for three years (2003–2005) in Corvallis, Oreg. and harvested in late November to early January. The layers of 'Red Dragon' were moderately vigorous, and rooted with a higher frequency and produced more roots than most other contorted selections. Asexual reproduction was also performed by whip grafting in Corvallis, Oreg. in late spring 2004. 'Red Dragon' has been grafted on each of four rootstocks, namely: 'Barcelona,' 'Mortarella,' 'Dundee,' and 'Newberg.' 'Red Dragon' is also suitable for propagation by micropropagation. The unique features of this new *Corylus* are stable and reproduced true-to-type in successive generations of asexual reproduction.

SUMMARY OF THE INVENTION

The following traits have been observed and are determined to be the unique characteristics of 'Red Dragon.' These characteristics in combination distinguish 'Red Dragon' as a new and distinct cultivar:

1. Outwardly spreading plant habit.
2. Twisting stems.
3. Rich dark burgundy-colored developing leaves and rich dark burgundy-colored fully expanded leaves during the spring and summer.
4. Burgundy color of the catkins and leaf buds.
5. Resistance to eastern filbert blight caused by the fungus *Anisogramma anomala* (Peck) E. Muller.
6. Presence of random amplified polymorphic DNA markers 152-800 and 268-580 in DNA of 'Red Dragon' amplified by polymerase chain reaction (PCR). These two markers are linked to a dominant allele for resistance to eastern filbert blight from the cultivar 'Gasaway,' not patented.

7. Expression of incompatibility alleles $S_6$ and $S_{26}$ in the styles.
8. DNA fingerprints at 20 of 28 microsatellite marker loci differ from two plants of 'Red Majestic' (U.S. Plant Pat. No. 16,048).

In side-by-side comparisons conducted in Corvallis, Oreg., plants of the new *Corylus* differed from plants of the *Corylus avellena* cultivar 'Contorta,' not patented, and other cultivars and selections of *Corylus avellena* known to the inventors primarily in leaf coloration and plant size as plants of the cultivar 'Contorta' and other cultivars and selections of *Corylus avellana* had green-colored leaves and were larger than plants of the new *Corylus*. 'Red Dragon' leaves retain their dark red color better than 'Red Majestic' (U.S. Plant Pat. No. 16,048). The DNA fingerprint of 'Red Dragon' differs from that of two plants of 'Red Majestic.' Furthermore, 'Red Dragon' has contorted growth habit whereas both parents have standard growth habit.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a typical plant of 'Red Dragon' in Corvallis, Oreg.

The photograph on the second sheet is a close-up view of a typical plant of 'Red Dragon.'

The photograph on the third sheet is a close-up view of the leaves of a typical plant of 'Red Dragon.'

DETAILED DESCRIPTION OF THE INVENTION

The cultivar 'Red Dragon' has not been observed under all possible environmental conditions. The phenotype may vary somewhat with variations in environment such as temperature and light intensity, without, however, any variance in genotype. The aforementioned photographs and following observations and measurements describe plants grown in Corvallis, Oreg. under commercial practice outdoors in the field during the fall, winter, and spring. Plants used for the photographs and description were about four years old. In the following description, color references are made to The Royal Horticultural Society Colour Chart, 1966 Edition, except where general terms of ordinary dictionary significance are used.

Botanical classification: *Corylus avellana* cultivar 'Red Dragon.'

Parentage:

*Female, or seed, parent.*—*Corylus avellana* selection OSU 487.055, not patented.

*Male, or pollen, parent.*—*Corylus avellana* selection OSU 367.039, not patented.

Propagation:

*Type.*—Rooted suckers.

*Time to initiate roots.*—About 30 days at 20° C.

*Time to produce a rooted young plant.*—About six months at 22° C.

*Root description.*—Fine to thick; freely branching; creamy white in color.

*Type.*—Whip grafting.

*Time to budbreak on the scions.*—About 14 days at 25° C.

*Time to produce a grafted plant.*—About six months at 25° C.

Plant description:

*General appearance.*—Perennial shrub. Outwardly spreading plant habit.

*Growth and branching habit.*—Freely branching; about 15 lateral branches develop per plant. Pinching, i.e., removal of the terminal apices, enhances branching with lateral branches potentially forming at every node. Strong and moderately vigorous growth habit. Stems twisting or "contorted."

*Plant height.*—About 2 meters.

*Plant diameter or spread.*—About 2 meters.

*Lateral branch description.*—Length: About 15 cm. Diameter: About 5 mm. Internode length: About 1.3 cm. Texture: Smooth, glabrous. Strength: Strong. Color, immature: 178A. Color, mature: 137A.

Foliage description:

*Arrangement.*—Alternate, simple.

*Length.*—About 12 cm.

*Width.*—About 10 cm.

*Shape.*—Oblong to ovate.

*Apex.*—Obtuse to acute.

*Base.*—Cordate.

*Margin.*—Serrate.

*Texture, upper and lower surfaces.*—Slightly pubescent.

*Venation pattern.*—Pinnate.

*Color.*—Developing foliage, upper and lower surfaces: 187A. Fully expanded foliage, upper surface: Spring and summer, 183B; late summer and fall, 137A. Fully expanded foliage, lower surface: Spring and summer, 178A; late summer and fall, 137A. Venation, upper surface: Spring and summer, 183B; late summer and fall, 137A. Venation, lower surface: Spring and summer, 178A; late summer and fall, 138B.

*Petiole.*—Length: About 1 cm. Diameter: About 2.5 mm. Texture, upper and lower surfaces: Pubescent. Color, upper surface: Spring and summer, 183B; late summer and fall, 137A. Color, lower surface: Spring and summer, 178A; late summer and fall, 138B.

*Leaf bud.*—Average length: About 6.5 mm. Average width: About 4.2 mm. Color: 178B.

Flower description: Male inflorescences are catkins, color prior to elongation 176B. The average length of the catkin is about 25 mm and the average width of the catkin is about 6 mm. The pollen color is yellow (RHS Canary Yellow 2/1). The female inflorescence are modified leaf buds and have an average length of about 6.5 mm and an average width of about 4.2 mm. Female inflorescence bud color is the same as leaf buds (178B) . Female inflorescence style color is purplish red (183B) . The peduncle is tan (165D) and the average peduncle length is 3 to 6 mm. The surface texture of the peduncle is matte (not glossy).

Disease/pathogen/pest resistance: Plants of the new *Corylus* are resistant to eastern filbert blight caused by the fungus *Anisogramma anomala* (Peck) E. Muller. Plants of the new *Corylus* are moderately susceptible to bud mites (*Phytoptus avellanae* Nal.) as are plants of 'Contorta.'

Temperature tolerance: Plants of the new *Corylus* have been observed to tolerate temperatures from about −10° C. to about 38° C. in the field in Corvallis, Oreg.

Trees of 'Red Dragon' set a moderate number of catkins (rating=2.3) which is less than 'Contorta' (rating=3.2) but more than other contorted selections. The catkins elongate in late winter with 'Contorta.''Red Dragon' has incompatibility alleles $S_6$ and $S_{26}$ as determined by fluorescence microscopy. Both alleles are expressed in the females, but only $S_6$ is expressed in the pollen because of dominance. Female inflorescences of 'Red Dragon' also emerge late in the season, with 'Contorta.' 'Red Dragon' trees will set a few nuts if its stigmas receive compatible pollen while receptive. The nuts are small, slightly long and compressed. The nuts are borne in clusters of one or two in husks equal in length to the nuts. Pollen of the red-leaf cultivars 'Rode Zeller' and 'Fusco Rubra' expresses $S_6$ and, thus, is incompatible. 'Contorta' ($S_5$ $S_{10}$) is reciprocally compatible with 'Red Dragon.'

DNA was extracted from several contorted seedlings and amplified by PCR. Random amplified polymorphic DNA (RAPD) markers UBC 152-800 and UBC 268-580, which flank the 'Gasaway' resistance gene, are present in 'Red Dragon.' RAPD marker AA12-850, which co-segregates with resistance, is also present. Scions were collected from 'Red Dragon' and several other contorted selections and three trees of each were grafted to rooted layers of *Corylus avellana*. The shoot tips of the grafted trees were inoculated in the greenhouse with a spore suspension of *Anisogramma anomala* and then held under high humidity. The three inoculated trees of 'Red Dragon' remained free of disease, while those of other selections in the same test developed cankers. The lack of cankers confirmed the results of the RAPD markers and indicates complete resistance to eastern filbert blight.

Notably, no trees have been lost to bacterial blight caused by *Xanthomonas campestris* pv. *corylina,* however susceptibility to the disease has not been rigorously tested.

Susceptibility to big bud mite (primarily *Phytoptus avellanae* Nal.) was rated after leaf fall once per year for three years. The scale was from 1 (no blasted buds) to 5 (many blasted buds). The average bud mite rating for 'Red Dragon' (3.2) is slightly higher than for 'Contorta' (2.6), but the difference is not significant at P=0.05. The nursery trade does not consider bud mite to be a serious problem for 'Contorta.' Therefore, bud mite should also not be a serious problem for 'Red Dragon.'

Fingerprinting with simple sequence repeat (SSR) markers was also performed. A panel of simple sequence repeat marker loci for hazelnut has been developed. Using primers designed for each SSR locus, hazelnut DNA was amplified by PCR as described (Bassil et al. (2005) J. Amer. Soc. Hort. Sci., 130:543-549). The sequences of the primers are provided in Table 1. Forward primers were fluorescently labeled with FAM, HEX, or NED, and the size of the amplified fragment was determined by capillary electrophoresis on an ABI 3100 instrument (Applied Biosystems; Foster City, Calif.). 93 SSR loci were used to amplify 32 hazelnut genotypes. Microsatellite markers in hazelnut are described in Bassil et al. (J. Amer. Soc. Hort. Sci. (2005) 130:543-549), Bassil et al. (Acta Horticulturae (2005) 686:105-110), Boccacci et al. (Mol. Ecol. Notes (2005) 5:934-937), Boccacci et al. (Genome (2006) 49:598-611), and Mehlenbacher et al. (Genome (2005) 49:122-133). The disclosure of each of the above citations is incorporated by reference herein.

TABLE 1

Microsatellite markers used to fingerprint 'Red Dragon' and other hazelnuts.

| Locus | Forward Primer Sequence | Reverse Primer Sequence |
|---|---|---|
| A040 | TGCTCAAGCAAATATTGCAC | GTTTGGGATCCAATTAACCCTCT |
| AJ490 | ACTGCAGCCCTTCAACTACG | AACGCCTACCTCATGTTTGG |
| B107 | GTAGGTGCACTTGATGTGCTTTAC | AACACCATATTGAGTCTTTCAAAGC |
| B507 | CTAAGCTCACCAAGAGGAAGTTGAT | GCTTCTGGGTCTCCTGCTCA |
| B508 | GGTCAAGATTTGATAAAGTGGGA | GCACTCCACTTGTGCGTTTTC |
| B617 | TCCGTGTTGAGTATGGACGA | TGTTTTTGGTGGAGCGATG |
| B619 | AGTCGGCTCCCCTTTTCTC | GCGATCTGACCTCATTTTTG |
| B643 | CCAGGTAAGCAGCTCAGTGT | ACCTCCCATTTGTGTCTTGC |
| B662 | CGAAAGATGGACTTCCATGAC | CAAGTTGAGATTCTTCCTGCAA |
| B709 | CCAAGCACGAATGAACTCAA | GCGGGTTCTCGTTGTACACT |
| B720 | CTCTGTGTCGGCTTTCTGGT | ATAAACCTCACGCCACACCT |
| B732 | GCCCTTCTTCTTTTCTGCAA | AGTGCCACCTCAACAAATCC |
| B733 | CACCCTCTTCACCACCTCAT | CATCCCCTGTTGGAGTTTTC |
| B741 | GTTCACAGGCTGTTGGGTTT | CGTGTTGCTCATGTGTTGTG |
| B774 | GTTTTGCGAGCTCATTGTCA | TGTGTGTGGTCTGTAGGCACT |
| B776 | TGTATGTACACACGGAGAGAGAGA | TGAGGGGAAGAGGTTTGATG |
| C010 | GGAGCCACCATGAAATTATACA | CACTTATTGCGATTGGTTCA |

TABLE 1-continued

Microsatellite markers used to fingerprint 'Red Dragon' and other hazelnuts.

| | | |
|---|---|---|
| C028 | CTACCCCATCGCTTGACAC | GGAGACTTGTTTGCCACAGA |
| C119 | CTCACCTTTACCCCTTCATTTT | GTTTCCTCATCTTCTGAGAACCATC |
| C504 | GGTCTCCTTCGCTAACATAACCAA | GTTGCCCTCGAGTTGTAGTA |
| K27-28-30 | ACACACACACACACACGAA | GCACCAAGCAGAACAATC |
| K74-1-19 | CTTACAGATAAATGGCTCAAA | AAGCAAGAAAGGGATGGT |
| K74-2-36 | AGGCATCAGTTCATCCAA | GGAAGGTGAGAGAAATCAAGT |
| K74-6-19 | TTATTCCACCAAAGTCTACCTC | TCCTCACCAATCACACTATTT |
| K76-1-26 | AAGGCGGCACTCGCTCAC | GAACAACTGAAGACAGCAAAG |
| K80-1-2 | CTGGCTTCAAATCAATCATAC | GAGGAGAGGAGAGAGAAAGAG |

| Locus | Repeat Motif | Size | Tm | SEQ ID NO (F, R) |
|---|---|---|---|---|
| A040 | $(CA)_{13}$ | 234-248 | 62 | 1, 2 |
| AJ490 | (CT)14Ns(CT)15 | 210-224 | 60 | 3, 4 |
| B107 | $(CT)_{14}$ | 112-151 | 58 | 5, 6 |
| B507 | (GA)1GC(GA)2GC(GA)14 | 182-202 | 55 | 7, 8 |
| B508 | $(GA)_{10}$ | 142-167 | 62 | 9, 10 |
| B617 | $(GA)_{15}$ | 280-298 | 60 | 11, 12 |
| B619 | $(TC)_{21}$ | 146-180 | 60 | 13, 14 |
| B643 | $(AG)_{13}$ | 180-196 | 60 | 15, 16 |
| B662 | $(TC)_{15}$ | 220-236 | 60 | 17, 18 |
| B709 | $(GA)_{21}$ | 219-233 | 60 | 19, 20 |
| B720 | $(AG)_{14}$ | 159-179 | 60 | 21, 22 |
| B732 | $(GA)_{13}$ | 140-156 | 60 | 23, 24 |
| B733 | $(TC)_{15}$ | 161-183 | 60 | 25, 26 |
| B741 | $(GT)_5(GA)_{12}$ | 176-194 | 60 | 27, 28 |
| B774 | $(AG)_{15}$ | 195-213 | 60 | 29, 30 |
| B776 | $(GA)_{17}$ | 134-148 | 60 | 31, 32 |
| C010 | $(GAA)^a$ | 272-319 | 58 | 33, 34 |
| C028 | $(GAA)_{10}$ | 131-147 | 60 | 35, 36 |
| C119 | $(GA)_7(GA)_9$ | 256-264 | 62 | 37, 38 |
| C504 | (CT)18 | 161-187 | 55 | 39, 40 |
| K27-28-30 | $(AG)_{10}$ | 328-345 | 57 | 41, 42 |
| K74-1-19 | $(AAAT)_5$ | 255-249 | 54 | 43, 44 |
| K74-2-36 | $(AGG)_7$ | 328-346 | 55 | 45, 46 |
| K74-6-19 | $(AG)_{15}$ | 366-393 | 56 | 47, 48 |

TABLE 1-continued

Microsatellite markers used to fingerprint 'Red Dragon' and other hazelnuts.

| | | | | |
|---|---|---|---|---|
| K76-1-26 | $(GA)_{17}$ | 240-278 | 58 | 49, 50 |
| K80-1-2 | $(GA)_{13}$ | 188-211 | 57 | 51, 52 |

Shown for each microsatellite marker locus are the sequence of the forward and reverse primers, the repeat motif, the range of sizes generated, the annealing temperature, and the sequence identifiers.

[d] $(GAA)_7GGA(GAA)_2N_{21}(GAA)_2ATT(GAA)_4N_{15}(GAA)_3$.

The allele sizes at 26 loci that distinguish 12 hazelnut genotypes are presented below (Table 2). OSU 217.094 is a red leaf seedling of 'Contorta,' and its pollen parent is believed to be 'Rode Zeller.' DNA of six contorted red leaf selections (two selections of the 'Red Majestic,' 'Red Dragon,' OSU 897.046, OSU 897.071 and OSU 897.082) was also amplified. 'Red Majestic' plants from Spring Meadow and from Klehm are clearly different, as they have different alleles at 19 of the 26 loci. Notably, 'Red Dragon' is different from both clones of 'Red Majestic' and from all other genotypes in Table 2. Indeed, 'Red Dragon' was found to exhibit different allele sizes at certain loci that allowed for it to be distinguish from other hazelnut genotypes such as 'Contorta' and 'Red Majestic.'

TABLE 2

Allele sizes at 26 microsatellite loci of 12 hazelnut genotypes.

| Genotype Locus | A040 | AJ490 | B107 | B507 | B508 |
|---|---|---|---|---|---|
| Gasaway | 238/246 | 218/222 | 122/128 | 179/190 | 147/165 |
| Rode Zeller | 238/246 | 214/216 | 134/144 | 189/197 | 149/149 |
| OSU 217.094 | 238/246 | 214/214 | 130/134 | 185/197 | 157/157 |
| Contorta | 246/246 | 212/214 | 122/130 | 185/189 | 147/155 |
| Red Majestic Spring Meadow | 246/246 | 212/212 | 122/130 | 189/189 | 147/157 |
| Red Majestic Klehm | 246/246 | 214/214 | 122/130 | 189/189 | 147/149 |
| OSU 897.046 | 238/246 | 212/214 | 128/134 | 179/197 | 147/157 |
| OSU 897.071 | 246/246 | 214/224 | 122/130 | 179/197 | 157/165 |
| Red Dragon (OSU 897.078) | 246/246 | 212/216 | 128/130 | 185/189 | 165/165 |
| OSU 897.082 | 246/246 | 212/216 | 122/134 | 179/185 | 165/165 |
| FuscoRubra | 238/248 | 214/222 | 120/122 | 189/199 | 165/165 |
| Barcelona | 236/236 | 212/224 | 112/134 | 181/191 | 157/157 |

| Genotype Locus | B617 | B619 | B643 | B662 | B709 |
|---|---|---|---|---|---|
| Gasaway | 292/296 | 170/174 | 190/196 | 230/236 | 227/227 |
| Rode Zeller | 282/292 | 166/176 | 192/192 | 230/230 | 227/227 |
| OSU 217.094 | 292/294 | 170/176 | 190/190 | 230/236 | 227/227 |
| Contorta | 282/294 | 156/170 | 182/192 | 232/236 | 221/227 |
| Red Majestic Spring Meadow | 282/282 | 156/170 | 192/192 | 226/232 | 227/227 |
| Red Majestic Klehm | 282/294 | 170/176 | 186/196 | 226/232 | 221/227 |
| OSU 897.046 | 294/294 | 156/176 | 182/192 | 230/230 | 227/227 |
| OSU 897.071 | 282/292 | 156/166 | 182/192 | 226/236 | 221/227 |
| Red Dragon (OSU 897.078) | 282/292 | 156/156 | 182/192 | 226/236 | 225/227 |
| OSU 897.082 | 282/292 | 156/156 | 190/196 | 232/236 | 221/227 |
| FuscoRubra | 290/296 | 156/166 | 182/192 | 222/228 | 225/227 |
| Barcelona | 286/290 | 156/170 | 190/190 | 230/232 | 225/233 |

| Genotype Locus | B720 | B732 | B733 | B741 | B774 |
|---|---|---|---|---|---|
| Gasaway | 161/163 | 140/154 | 173/173 | 186/188 | 203/209 |
| Rode Zeller | 159/167 | 150/150 | 173/173 | 178/184 | 203/207 |
| OSU 217.094 | 167/167 | 150/154 | 161/173 | 178/184 | 203/203 |

TABLE 2-continued

| | | | | | |
|---|---|---|---|---|---|
| Contorta | 159/167 | 142/154 | 161/161 | 163/184 | 203/203 |
| Red Majestic Spring Meadow | 167/167 | 142/142 | 161/161 | 178/184 | 203/203 |
| Red Majestic Klehm | 159/167 | 140/140 | 161/161 | 163/178 | 203/209 |
| OSU 897.046 | 163/167 | 140/154 | 161/161 | 178/186 | 203/209 |
| OSU 897.071 | 159/159 | 140/154 | 161/161 | 163/178 | 203/203 |
| Red Dragon (OSU 897.078) | 163/167 | 140/150 | 161/161 | 178/178 | 203/209 |
| OSU 897.082 | 159/167 | 140/150 | 161/161 | 163/178 | 203/203 |
| FuscoRubra | 165/171 | 146/150 | 173/183 | 178/186 | 197/213 |
| Barcelona | 161/167 | 150/154 | 171/173 | 177/186 | 203/207 |

| Genotype Locus | B776 | C101 | C028 | C119 | C504 |
|---|---|---|---|---|---|
| Gasaway | 144/148 | 281/281 | 144/144 | 258/264 | 161/164 |
| Rode Zeller | 134/136 | 275/278 | 132/141 | 256/264 | 158/164 |
| OSU 217.094 | 136/146 | 275/275 | 132/141 | 256/258 | 161/164 |
| Contorta | 134/146 | 281/281 | 132/132 | 258/264 | 158/161 |
| Red Majestic Spring Meadow | 134/146 | 275/275 | 132/141 | 258/264 | 158/161 |
| Red Majestic Klehm | 146/146 | 281/281 | 132/135 | 258/264 | 152/161 |
| OSU 897.046 | 136/148 | 275/275 | 141/144 | 256/258 | 161/161 |
| OSU 897.071 | 134/148 | 275/281 | 132/132 | 258/258 | 161/161 |
| Red Dragon (OSU 897.078) | 134/148 | 275/275 | 132/141 | 256/258 | 161/161 |
| OSU 897.082 | 146/148 | 275/281 | 132/141 | 258/258 | 161/161 |
| FuscoRubra | 134/136 | 278/278 | 135/135 | 256/264 | 152/164 |
| Barcelona | 134/136 | 275/278 | 132/141 | 258/258 | 155/155 |

| Genotype Locus | K27-28-30 | K74-1-19 | K74-2-36 |
|---|---|---|---|
| Gasaway | 331/333 | 239/248 | 337/346 |
| Rode Zeller | 329/331 | 234/234 | 340/343 |
| OSU 217.094 | 329/329 | 234/248 | 337/340 |
| Contorta | 331/331 | 239/248 | 337/337 |
| Red Majestic Spring Meadow | 329/331 | 239/248 | 337/337 |
| Red Majestic Klehm | 329/329 | 239/239 | 337/343 |
| OSU 897.046 | 331/331 | 234/248 | 337/340 |
| OSU 897.071 | 331/331 | 239/248 | 337/340 |
| Red Dragon (OSU 897.078) | 331/331 | 234/248 | 337/340 |
| OSU 897.082 | 331/331 | 234/248 | 337/337 |
| FuscoRubra | 329/329 | 248/248 | 337/346 |
| Barcelona | 329/331 | 234/248 | 337/337 |

| Genotype Locus | K74-6-19 | K76-1-26 | K80-1-2 |
|---|---|---|---|
| Gasaway | 378/390 | 255/259 | 194/197 |
| Rode Zeller | 392/392 | 253/255 | 201/201 |
| OSU 217.094 | 376/392 | 253/253 | 201/201 |
| Contorta | 376/376 | 253/255 | 201/203 |
| Red Majestic Spring Meadow | 376/392 | 253/255 | 203/203 |
| Red Majestic Klehm | 376/376 | 253/255 | 199/203 |
| OSU 897.046 | 376/390 | 253/253 | 197/201 |
| OSU 897.071 | 376/376 | 251/253 | 197/201 |

TABLE 2-continued

| | | | |
|---|---|---|---|
| Red Dragon (OSU 897.078) | 376/392 | 253/253 | 201/203 |
| OSU 897.082 | 376/390 | 253/253 | 197/201 |

TABLE 2-continued

| | | | |
|---|---|---|---|
| FuscoRubra | 380/392 | 255/265 | 197/207 |
| Barcelona | 374/378 | 259/265 | 203/205 |

SEQUENCE LISTING

<160> NUMBER OF SEQ ID NOS: 52

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1 tgctcaagca aatattgcac 20

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2 gtttgggatc caattaaccc tct 23

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3 actgcagccc ttcaactacg 20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4 aacgcctacc tcatgtttgg 20

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5 gtaggtgcac ttgatgtgct ttac 24

<210> SEQ ID NO 6
<211> LENGTH: 25
<212> TYPE: DNA
<213> ORGANISM: Artificial Sequence -continued <220> FEATURE:
<223> OTHER INFORMATION: Primer

<400> SEQUENCE: 6 aacaccatat tgagtctttc aaagc 25

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7 ctaagctcac caagaggaag ttgat 25

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8 gcttctgggt ctcctgctca 20

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9 ggtcaagatt tgataaagtg gga 23

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10 gcactccact tgtgcgtttt c 21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11 tccgtgttga gtatggacga 20

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12

-continued tgtttttggt ggagcgatg 19

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13 agtcggctcc ccttttctc 19

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14 gcgatctgac ctcatttttg 20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15 ccaggtaagc agctcagtgt 20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16 acctcccatt tgtgtcttgc 20

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17 cgaaagatgg acttccatga c 21

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18 caagttgaga ttcttcctgc aa 22

<210> SEQ ID NO 19
<211> LENGTH: 20

-continued

<212> TYPE: DNA
<213> ORGANISM: Artificial Sequence
<220> FEATURE:
<223> OTHER INFORMATION: Primer

<400> SEQUENCE: 19 ccaagcacga atgaactcaa 20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20 gcgggttctc gttgtacact 20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21 ctctgtgtcg gctttctggt 20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22 ataaacctca cgccacacct 20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23 gcccttcttc ttttctgcaa 20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24 agtgccacct caacaaatcc 20

<210> SEQ ID NO 25
<211> LENGTH: 20
<212> TYPE: DNA
<213> ORGANISM: Artificial Sequence
<220> FEATURE:
<223> OTHER INFORMATION: Primer -continued

<400> SEQUENCE: 25 caccctcttc accacctcat 20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26 catcccctgt tggagttttc 20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27 gttcacaggc tgttgggttt 20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28 cgtgttgctc atgtgttgtg 20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29 gttttgcgag ctcattgtca 20

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30 tgtgtgtggt ctgtaggcac t 21

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31 tgtatgtaca cacggagaga gaga 24

-continued

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32 tgaggggaag aggtttgatg 20

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33 ggagccacca tgaaattata ca 22

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34 cacttattgc gattggttca 20

<210> SEQ ID NO 35
<211> LENGTH: 19
<212> TYPE: DNA
<213> ORGANISM: Artificial Sequence
<220> FEATURE:
<223> OTHER INFORMATION: Primer

<400> SEQUENCE: 35 ctaccccatc gcttgacac 19

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36 ggagacttgt ttgccacaga 20

<210> SEQ ID NO 37
<211> LENGTH: 22
<212> TYPE: DNA
<213> ORGANISM: Artificial Sequence
<220> FEATURE:
<223> OTHER INFORMATION: Primer

<400> SEQUENCE: 37 ctcaccttta ccccttcatt tt 22

<210> SEQ ID NO 38
<211> LENGTH: 25
<212> TYPE: DNA
<213> ORGANISM: Artificial Sequence
<220> FEATURE:

-continued

<223> OTHER INFORMATION: Primer

<400> SEQUENCE: 38 gtttcctcat cttctgagaa ccatc 25

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39 ggtctccttc gctaacataa ccaa 24

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40 gttgccctcg agttgtagta 20

<210> SEQ ID NO 41
<211> LENGTH: 19
<212> TYPE: DNA
<213> ORGANISM: Artificial Sequence
<220> FEATURE:
<223> OTHER INFORMATION: Primer

<400> SEQUENCE: 41 acacacacac acacacgaa 19

<210> SEQ ID NO 42
<211> LENGTH: 18
<212> TYPE: DNA
<213> ORGANISM: Artificial Sequence
<220> FEATURE:
<223> OTHER INFORMATION: Primer

<400> SEQUENCE: 42 gcaccaagca gaacaatc 18

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43 cttacagata aatggctcaa a 21

<210> SEQ ID NO 44
<211> LENGTH: 18
<212> TYPE: DNA
<213> ORGANISM: Artificial Sequence
<220> FEATURE:
<223> OTHER INFORMATION: Primer

<400> SEQUENCE: 44 aagcaagaaa gggatggt 18

-continued

<210> SEQ ID NO 45
<211> LENGTH: 18
<212> TYPE: DNA
<213> ORGANISM: Artificial Sequence
<220> FEATURE:
<223> OTHER INFORMATION: Primer

<400> SEQUENCE: 45 aggcatcagt tcatccaa 18

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46 ggaaggtgag agaaatcaag t 21

<210> SEQ ID NO 47
<211> LENGTH: 22
<212> TYPE: DNA
<213> ORGANISM: Artificial Sequence
<220> FEATURE:
<223> OTHER INFORMATION: Primer

<400> SEQUENCE: 47 ttattccacc aaagtctacc tc 22

<210> SEQ ID NO 48
<211> LENGTH: 21
<212> TYPE: DNA
<213> ORGANISM: Artificial Sequence
<220> FEATURE:
<223> OTHER INFORMATION: Primer

<400> SEQUENCE: 48 tcctcaccaa tcacactatt t 21

<210> SEQ ID NO 49
<211> LENGTH: 18
<212> TYPE: DNA
<213> ORGANISM: Artificial Sequence
<220> FEATURE:
<223> OTHER INFORMATION: Primer

<400> SEQUENCE: 49 aaggcggcac tcgctcac 18

<210> SEQ ID NO 50
<211> LENGTH: 21
<212> TYPE: DNA
<213> ORGANISM: Artificial Sequence
<220> FEATURE:
<223> OTHER INFORMATION: Primer

<400> SEQUENCE: 50 gaacaactga agacagcaaa g 21

<210> SEQ ID NO 51
<211> LENGTH: 21
<212> TYPE: DNA

-continued

```
<213> ORGANISM: Artificial Sequence
<220> FEATURE:
<223> OTHER INFORMATION: Primer

<400> SEQUENCE: 51

ctggcttcaa atcaatcata c                                              21


<210> SEQ ID NO 52
<211> LENGTH: 21
<212> TYPE: DNA
<213> ORGANISM: Artificial Sequence
<220> FEATURE:
<223> OTHER INFORMATION: Primer

<400> SEQUENCE: 52

gaggagagga gagagaaaga g                                              21
```

What is claimed is:

1. A new and distinct *Corylus* plant named 'Red Dragon' as illustrated and described.

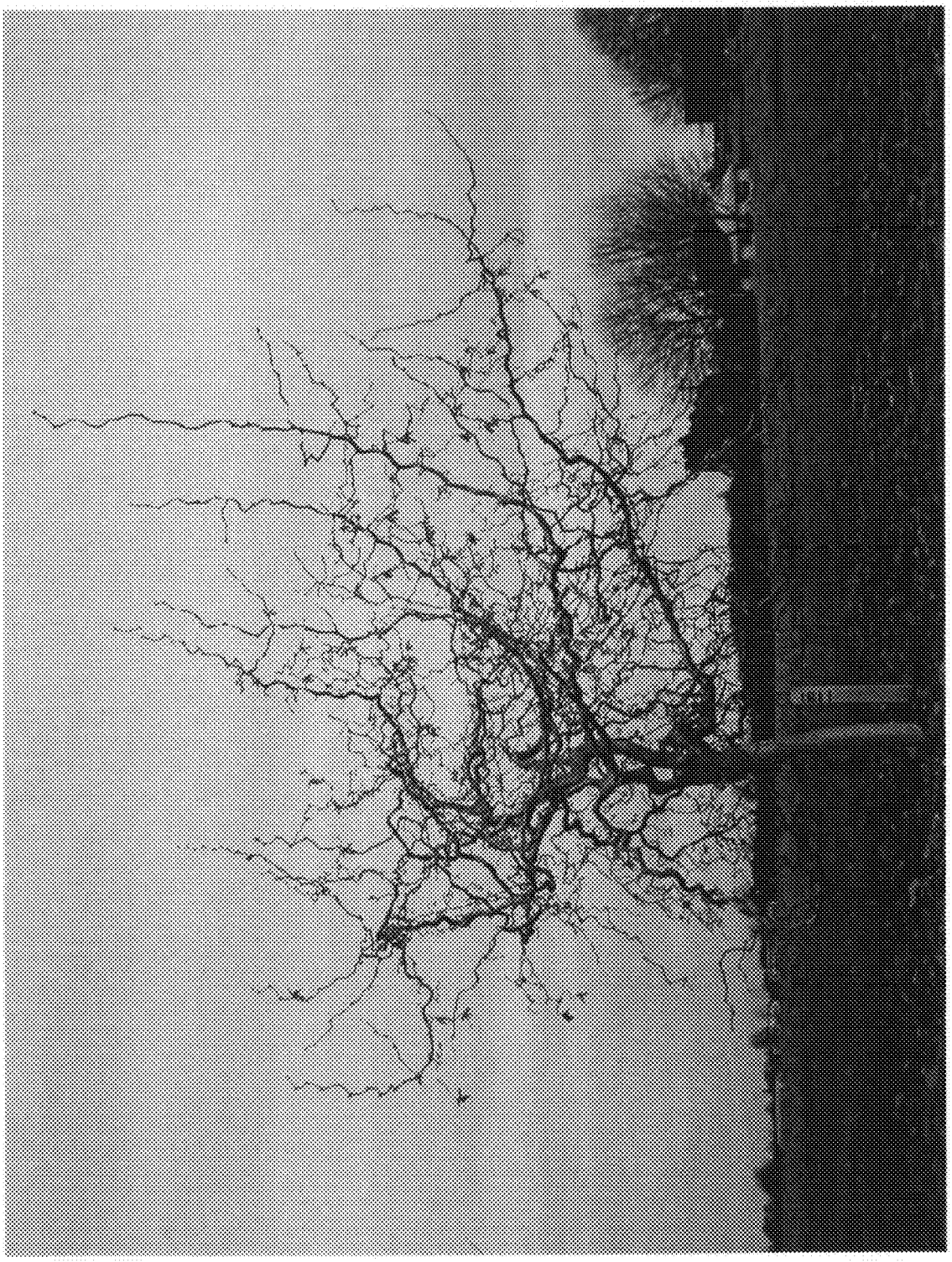

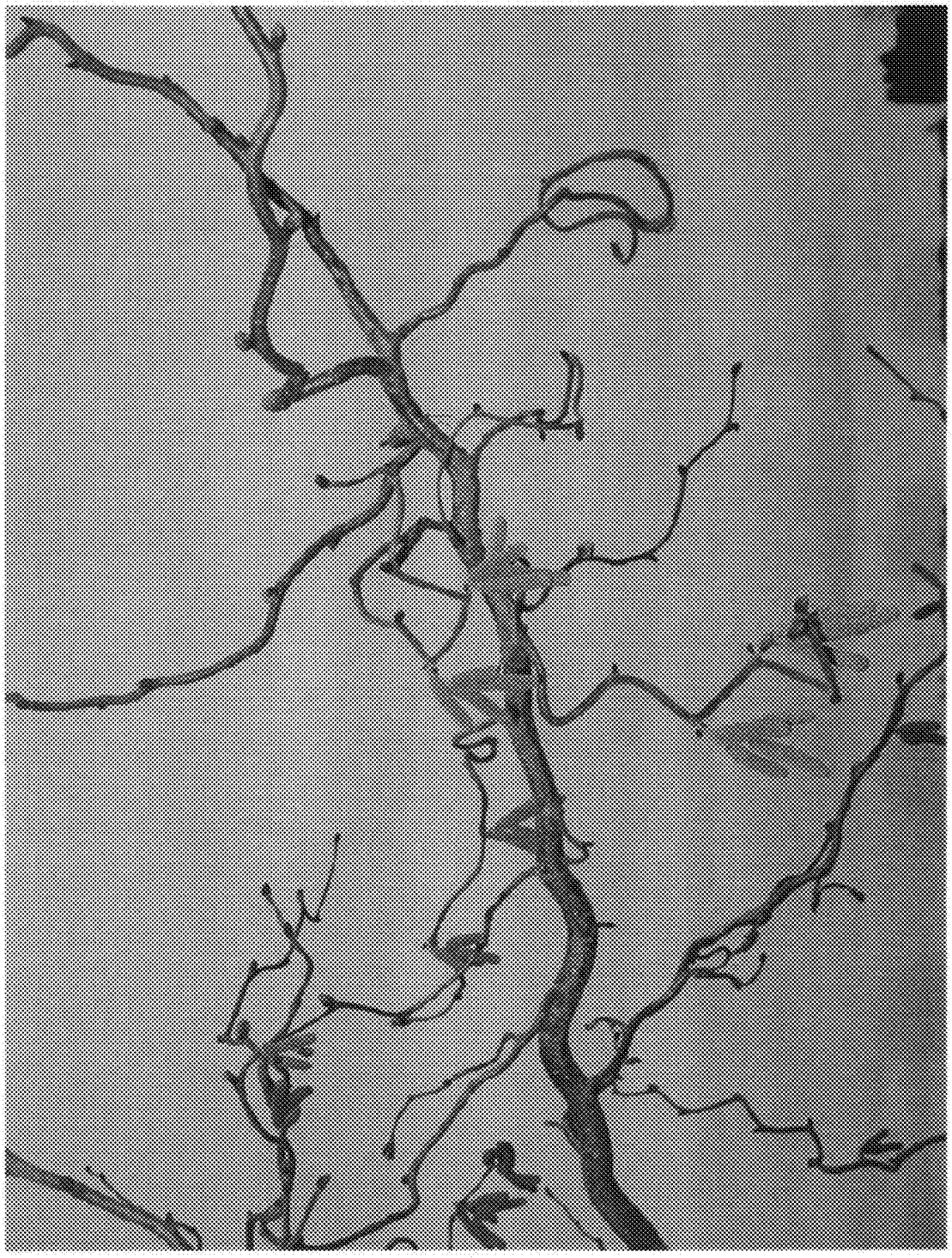

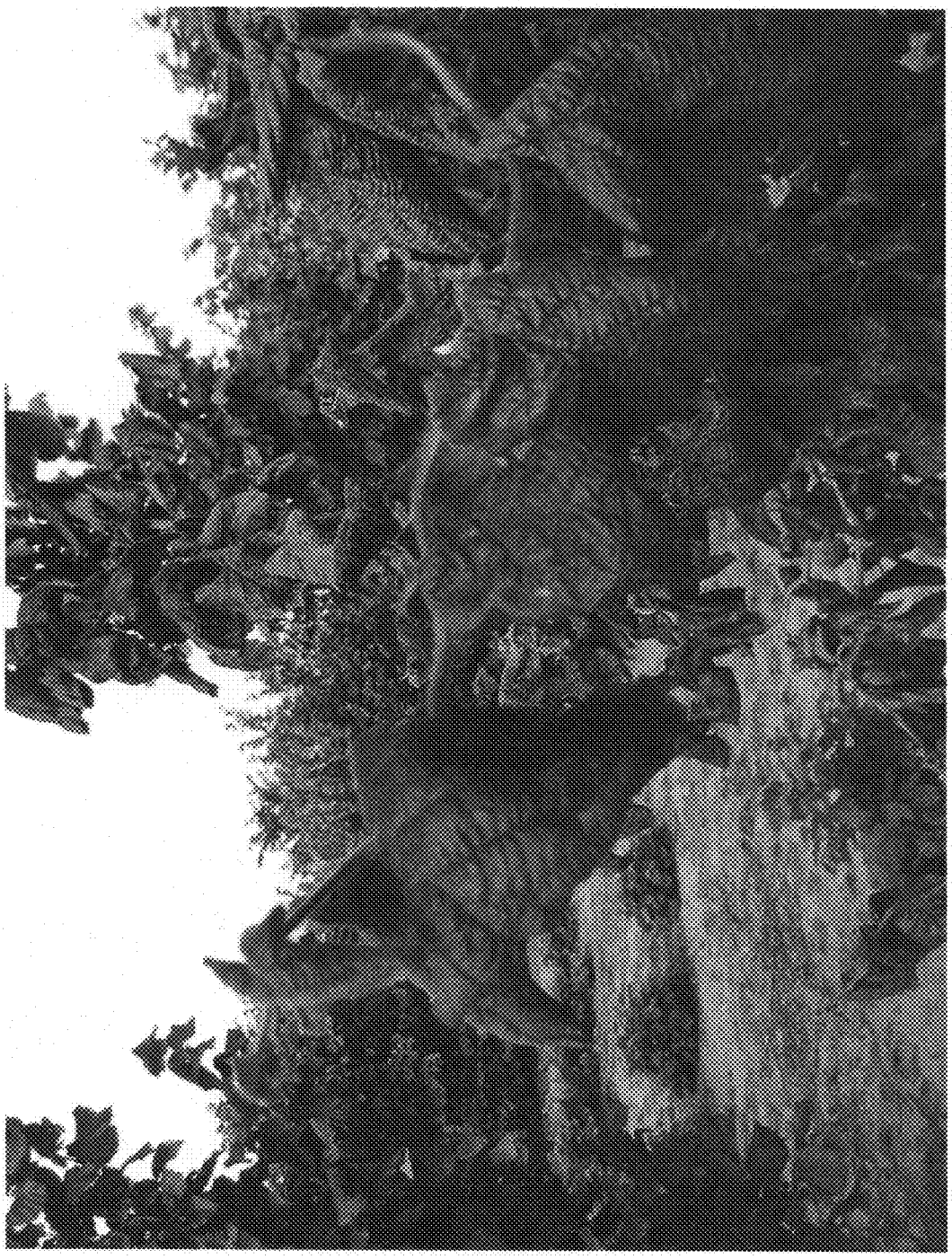

* * * * *